United States Patent [19]

Fujita

[11] 4,376,871

[45] Mar. 15, 1983

[54] METHOD FOR PURIFICATION OF CYCLOPENTENOLONES

[75] Inventor: Fumio Fujita, Ibaraki, Japan

[73] Assignee: Sumitomo Chemical Co., Limited, Osaka, Japan

[21] Appl. No.: 372,379

[22] Filed: Apr. 27, 1982

[30] Foreign Application Priority Data

Apr. 30, 1981 [JP] Japan ................................ 56-66682

[51] Int. Cl.$^3$ ............................................. C07C 45/85
[52] U.S. Cl. .................................................. 568/366
[58] Field of Search ................................ 568/410, 366

[56] References Cited

U.S. PATENT DOCUMENTS

| | | | |
|---|---|---|---|
| 2,813,905 | 11/1957 | Lyons et al. | 568/366 |
| 3,161,684 | 12/1964 | Wilkinson et al. | 568/410 |
| 3,536,495 | 10/1970 | Fly et al. | 568/366 |

OTHER PUBLICATIONS

Yuki, Chem. Abst., vol. 94, 103,148Z (1981).
Sharpless, J. Org. Chem., vol. 40(9), pp. 1253-1257 (1975).

*Primary Examiner*—James H. Reamer
*Attorney, Agent, or Firm*—Cushman, Darby & Cushman

[57] ABSTRACT

Purification of cyclopentenolone such as, for example, 2-propargyl-3-methyl-4-hydroxy-2-cyclopenten-1-one, which is an intermediate to manufacture pyrethroidal insecticides, is made by reacting with calcium chloride to form the cyclopentenolone-calcium chloride complex and then decomposing the complex with water.

6 Claims, No Drawings

METHOD FOR PURIFICATION OF CYCLOPENTENOLONES

The present invention relates to the method for the purification of cyclopentenolones. More particularly, the present invention relates to the method for purifying cyclopentenolones comprising reacting a cyclopentenolone of the formula (I),

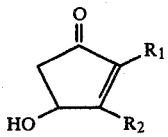

(wherein $R_1$ represents a $C_{1-4}$ alkyl, $C_{3-4}$ alkenyl, $C_{3-4}$ alkynyl or phenyl $C_{1-4}$ alkyl group, and $R_2$ represents hydrogen atom or a $C_{1-4}$ alkyl group), with calcium chloride, preferably in an organic solvent, separating the formed cyclopentenolone-calcium chloride complex from the reaction mixture, and decomposing the complex with water to obtain the purified cyclopentenolone.

The cyclopentenolones representable by the formula (I) are useful intermediates to manufacture pyrethroidal insecticides (see, for example, U.S. Pat. Nos. 3,636,059, 3,876,681, 3,934,023, etc.). They can be derived to various insecticides, through esterification reaction with chrysanthemic acid and various other pyrethroidal acid moieties.

When the purity of the cyclopentenolone to be employed herein is not so high, there may be troubles, such as hindrance to the esterification reaction and decrease in the purity of the resulting pyrethroid. Thus, the cyclopentenolone having a purity as high as possible is desired, for the material to be derived to pyrethroidal insecticide. The cyclopentenolones manufactured according to the conventional method include a number of impurities having lower or higher boiling points, which have to be removed by any of purification processes. Heretofore, a fractional distillation has generally been conducted for such purification. However, the fractional distillation necessitates a highly efficient rectifier, which imposes many restrictions on the equipment. When a large amount of material is to be handled, especially in batch system, fractional distillation is not applicable to a compound which is unstable against heat.

Most of cyclopentenolones are unstable to heat and inadequate to be subjected to fractional distillation, because they possess carbonyl and hydroxyl groups and unsaturated linkage, these being reactive functional groups. Thus, the purification of cyclopentenolones by fractional distillation has difficulties, when practiced in a commercial scale. Accordingly, development of an effective method for the purification of cyclopentenolones has been looked for.

The present inventor has been earnestly investigated on the solution of such demand, consequently, has found out a method of the purification which has a superior purification efficiency to that of fractional distillation, and has accomplished the present invention.

Thus, an object of the invention is to provide a method for purifying cyclopentenolones of the formula (I), by reacting a cyclopentenolone with calcium chloride, preferably in an organic solvent, separating the formed cyclopentenolone-calcium chloride complex from the reaction mixture, and decomposing the complex with water to obtain the cyclopentenolone in a high purity.

According to the method for the purification in the present invention, cyclopentenolones can be highly purified by exceedingly simple process with high efficiency. The method is extremely advantageous from the practical and economical points of view, particularly in a commercial scale operation.

The method for the purification in the present invention will be illustrated hereinafter. Calcium chloride employed in the present method may be anhydrous. When calcium chloride is employed as an aqueous or lower alcoholic solution, it may be anhydrous or hydrous. The amount used may ordinarily be 0.4 to 5 mol per mole of the cyclopentenolone. It may be employed in the form of powder or granules, or in the form of a solution in water or a lower alcohol, such as methanol and ethanol. In case where it is employed as a solution in water or a lower alcohol, the reaction can be completed by removing the water or the lower alcohol solvent during azeotropic distillation. There is no specific limitation to organic solvents employed for the present method, so far as they are inert to calcium chloride and the cyclopentenolone compounds. As the solvents generally employable, hydrocarbon solvents, such as benzene, toluene, xylene, hexane, heptane and the like, esters, such as methyl acetate, ethyl acetate and the like, lower aliphatic ketones, such as acetone, methyl ethyl ketone and the like, may be illustrated.

The reaction temperature is preferably from 0° to 150° C., since too low temperature necessitates longer period of time for the reaction, while too high temperature tends to cause coloration of the final product. The reaction time varies depending upon the reaction temperature, but 2 to 15 hours ordinarily secures the object.

Thereafter, the resulting cyclopentenolone-calcium chloride complex is separated by, for example, filtration. The complex is decomposed with an excess amount of water, to obtain cyclopentenolone in high purity.

The regenerated cyclopentenolone may be extracted with an organic solvent and recovered satisfactorily from the extract.

According to this method, crude cyclopentenolones of 70 to 80% purity can be converted to purified ones of 90% or higher purity, with a high purification yield. Thus, the method of the present invention is an exceedingly effective for the purification.

As the embodiment of the cyclopentenolones of the formula (I) mentioned above, 2-allyl-3-methyl-4-hydroxy-2-cyclopenten-1-one, 2-propargyl-3-methyl-4-hydroxy-2-cyclopenten-1-one, 2-benzyl-4-hydroxy-2-cyclopenten-1-one, 2-(1-methyl-2-propenyl)-4-hydroxy-2-cyclopenten-1-one, etc. may be illustrated.

Hereinafter, the present invention will more concretely be described with respect to the following working examples, in which the purity is according to gas chromatographic quantitative analysis using the internal standard.

EXAMPLE 1

Crude 2-propargyl-3-methyl-4-hydroxy-2-cyclopenten-1-one (7.51 g, 80.1% purity) and 22.2 g of powdered anhydrous calcium chloride were added into 80 g of toluene, and the mixture was stirred at 60° C. for 10 hours. The crystalline complex formed in the mixture was filtered and washed with toluene. Then, 30 g of water was added to decompose the complex, and the regenerated oily substance was extracted with ethyl acetate. The extract was concentrated, to give 5.89 g of purified 2-propargyl-3-methyl-4-hydroxy-2-cyclopenten-1-one (93.0% purity, 91% purification yield).

EXAMPLE 2

Using 7.6 g of crude 2-allyl-3-methyl-4-hydroxy-2-cyclopenten-1-one (allethrolone, 77.2% purity), with otherwise the similar procedure as in Example 1, 5.56 g of purified allethrolone (93.2% purity) was obtained (88.3% purification yield).

EXAMPLE 3

To a solution of 7.51 g of crude 2-propargyl-3-methyl-4-hydroxy-2-cyclopenten-1-one (80.1% purity) in 400 g of toluene was added a solution of 22.2 g of anhydrous calcium chloride in 90 g of methanol. The mixture was heated to remove the methanol azeotropically. During the course of the 8 hour distillation starting from boiling temperature of 64° C. with slow temperature rising up to 110° C., 200 g of a methanol-toluene mixture was distilled off. The formed crystalline complex was filtered and washed with toluene. The complex was decomposed with 30 g water, and the regenerated oily substance was extracted with ethyl acetate. The extract was concentrated to give 6.14 g of purified 2-propargyl-3-methyl-4-hydroxy-2-cyclopenten-1-one (90.0% purity, 91.5% purification yield).

EXAMPLE 4

To a solution of 17.50 g of crude 2-propargyl-3-methyl-4-hydroxy-2-cyclopenten-1-one (79.4% purity) in 39.38 g of ethyl acetate, under stirring at a room temperature, was added 9.04 g of powdered anhydrous calcium chloride portion-wise. After 3 hours, the formed crystalline complex was filtered and washed with ethyl acetate. The complex was decomposed with 24.50 g of water, and the regenerated oil substance was extracted with ethyl acetate. The extract was concentrated to give 13.14 g of purified 2-propargyl-3-methyl-4-hydroxy-2-cyclopenten-1-one (96.5% purity, 91.3% purification yield).

EXAMPLE 5

Using 17.50 g of crude 2-propargyl-3-methyl-4-hydroxy-2-cyclopenten-1-one (79.4% purity), 39.38 g of acetone and 9.04 g of powdered anhydrous calcium chloride, the similar procedure as in Example 4 was repeated. The formed crystalline complex was filtered and washed with acetone. The similar treatment as in Example 4 gave 8.55 g of purified 2-propargyl-3-methyl-4-hydroxy-2-cyclopenten-1-one (95.5% purity, 58.8% purification yield).

EXAMPLE 6

Using 15.00 g of crude 2-propargyl-3-methyl-4-hydroxy-2-cyclopenten-1-one (76.9% purity), 33.75 g of methyl ethyl ketone and 7.76 g of powdered anhydrous calcium chloride, the similar procedure as in Example 4 was repeated. The formed crystalline complex was filtered and washed with methyl ethyl ketone. The complex was decomposed with 21.00 g of water, and the regenerated oil substance was extracted with ethyl acetate. Concentration of the extract gave 8.04 g of purified 2-propargyl-3-methyl-4-hydroxy-2-cyclopenten-1-one (94.0% purity, 65.5% purification yield).

EXAMPLE 7

Using 17.50 g of crude 2-propargyl-3-methyl-4-hydroxy-2-cyclopenten-1-one (79.4% purity), 39.38 g of ethyl acetate and 7.76 g of granular anhydrous calcium chloride, with otherwise the similar procedure as in Example 4, 13.12 g of purified 2-propargyl-3-methyl-4-hydroxy-2-cyclopenten-1-one (96.3% purity) was obtained (90.9% purification yield).

EXAMPLE 8

To a solution of 25.0 g of 2-propargyl-3-methyl-4-hydroxy-2-cyclopenten-1-one (80.1% purity) in 400 g toluene was added a solution of 98.0 g of calcium chloride dihydrate in 60 g of water. The mixture was heated while stirring. At the beginning, water and toluene were distilled out at the azeotropic temperature of 84° C. After a while, the temperature slowly rose up to 111° C. Within 8 hours, 350 g of a water-toluene mixture was distilled off. The formed calcium chloride complex was filtered, and washed with toluene. The complex was decomposed with 90 g of water, and the regenerated oily substance was extracted with ethyl acetate. Concentration of the extract gave 19.22 g of purified 2-propargyl-3-methyl-4-hydroxy-2-cyclopenten-1-one (91.5% purity, 88.0% purification yield).

I claim:

1. A method for purifying cyclopentenolone comprising reacting a cyclopentenolone of the formula (I),

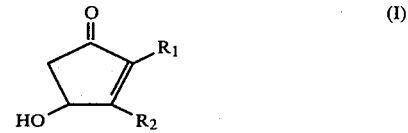

(wherein $R_1$ represents a $C_{1-4}$ alkyl, $C_{3-4}$ alkenyl, $C_{3-4}$ alkynyl or phenyl $C_{1-4}$ alkyl group, and $R_2$ represents hydrogen atom or a $C_{1-4}$ alkyl group), with calcium chloride, separating the formed cyclopentenolone-calcium chloride complex from the reaction mixture, and decomposing the complex with water to obtain the purified cyclopentenolone.

2. A method according to claim 1, wherein the calcium chloride is anhydrous calcium chloride.

3. A method according to claim 1, wherein the calcium chloride employed is hydrous or anhydrous calcium chloride in the form of a solution in water or a lower alcohol, and the water or the lower alcohol is removed by azeotropic distillation in the presence of an azeotropic organic solvent, to form the cyclopentenolone-calcium chloride complex.

4. A method according to claim 1, wherein the reaction is carried out in an organic solvent which is inert to calcium chloride and the cyclopentenolone.

5. A method according to claim 1, wherein the cyclopentenolone is 2-propargyl-3-methyl-4-hydroxy-2-cyclopenten-1-one.

6. A method according to claim 1, wherein the cyclopentenolone is 2-allyl-3-methyl-4-hydroxy-2-cyclopenten-1-one.

* * * * *